(12) United States Patent
Das

(10) Patent No.: US 11,231,368 B2
(45) Date of Patent: Jan. 25, 2022

(54) ULTRA LOW RANGE SULFITE MEASUREMENT

(71) Applicant: Hach Company, Loveland, CO (US)

(72) Inventor: Amit Das, Timnath, CO (US)

(73) Assignee: HACH COMPANY, Loveland, CO (US)

(*) Notice: Subject to any disclaimer, the term of this patent is extended or adjusted under 35 U.S.C. 154(b) by 250 days.

(21) Appl. No.: 16/425,173

(22) Filed: May 29, 2019

(65) Prior Publication Data

US 2020/0378893 A1 Dec. 3, 2020

(51) Int. Cl.
*G01N 21/64* (2006.01)
*G01N 21/77* (2006.01)
*G01N 33/18* (2006.01)

(52) U.S. Cl.
CPC .......... *G01N 21/643* (2013.01); *G01N 21/77* (2013.01); *G01N 33/182* (2013.01); *G01N 2021/6439* (2013.01); *G01N 2021/6443* (2013.01); *G01N 2021/7786* (2013.01); *G01N 2201/125* (2013.01); *Y10T 436/18* (2015.01)

(58) Field of Classification Search
CPC .. G01N 21/64; G01N 21/6428; G01N 21/643; G01N 21/77; G01N 2021/6439; G01N 2021/6443; G01N 2021/7786; G01N 33/182; Y10T 436/18
See application file for complete search history.

(56) References Cited

FOREIGN PATENT DOCUMENTS

CN 1534021 A * 10/2004 ......... H01L 51/0064
CN 105738640 A 7/2016

OTHER PUBLICATIONS

Zhang, Q. et al. "A near-infrared fluorescent probe for rapid, colorimetric and ratiometric detection of bisulfite in food, serum, and living cells," Sensors and Actuators B 211 (2015) 377-384 and Supplementary data. (Year: 2015).*
Fujii, S.-I. et al. "Fluorometric determination of sulfite and nitrite in aqueous samples using a novel detection unit of a microfluidic device," Analytical Sciences 2004; 20(1): 209-212 (Year: 2004).*
Li, H. "Rapidly responsive and highly selective fluorescent probe for sulfite detection in real samples and living cells," Analytics Chimica Acta 897 (2015) 102-108; including Supplementary data. (Year: 2015).*
Samanta, S. et al. "A ratiometric fluorogenic probe for the real-time detection of SO3 2− in aqueous medium: application in a cellulose paper based device," Analyst, 2018, 143, 250. Published on Nov. 8, 2017; including Electronic supplementary information (Year: 2017).*

(Continued)

*Primary Examiner* — Jennifer Wecker
*Assistant Examiner* — Michelle Adams
(74) *Attorney, Agent, or Firm* — Ference & Associates LLC

(57) ABSTRACT

An embodiment provides a method for measuring sulfite in a solution, including: preparing a hemicyanine indicator; introducing the hemicyanine indicator to a solution containing an amount of sulfite, wherein the hemicyanine indicator reacts with the sulfite and causes a change in fluorescence of the solution; and measuring the amount of sulfite in the solution by measuring an intensity of the fluorescence. Other aspects are described and claimed.

11 Claims, 5 Drawing Sheets

(56) References Cited

OTHER PUBLICATIONS

International Searching Authority, Notification of Transmittal of the International Search Report and the Written Opinion of the International Searching Authority, or the Declaration, dated Aug. 4, 2020, pp. 11.

Li Hongda "Rapidly responsive and highly selective fluorescent probe for sulfite detection in real samples and living cells", Analytica Chimica Acta, Els Ev I Er, Amsterdam, NL, vol. 897, Oct. 1, 2015 (Oct. 1, 2015), pp. 102-108.

* cited by examiner

ULTRA LOW RANGE SULFITE MEASUREMENT

BACKGROUND

This application relates generally to measuring sulfite ions in aqueous or liquid samples, and, more particularly, to the measurement of sulfite ions in low concentrations.

Ensuring water quality is critical in a number of industries such as pharmaceuticals and other manufacturing fields. Additionally, ensuring water quality is critical to the health and well-being of humans, animals, and plants which are reliant on the water for survival. One element that is typically measured is sulfite. Too much sulfite in water may be harmful to humans or animals, it can cause the water to have a bad taste or increased odor, and it can result in higher costs. Therefore, detecting the presence and concentration of sulfite in water or other liquid solutions is vital.

BRIEF SUMMARY

In summary, one embodiment provides a method for measuring sulfite in a solution, comprising: preparing a hemicyanine indicator; introducing the hemicyanine indicator to a solution containing an amount of sulfite, wherein the hemicyanine indicator reacts with the sulfite and causes a change in fluorescence of the solution; and measuring the amount of sulfite in the solution by measuring an intensity of the fluorescence.

Another embodiment provides a measurement device for measuring sulfite in a solution, comprising: a processor; and a memory storing instructions executable by the processor to: prepare a hemicyanine indicator; introduce the hemicyanine indicator to a solution containing an amount of sulfite, wherein the hemicyanine indicator reacts with the sulfite and causes a change in fluorescence of the solution; and measure the amount of sulfite in the solution by measuring an intensity of the fluorescence.

An further embodiment provides a method for measuring sulfite in a solution, comprising: preparing a hemicyanine indicator, wherein the hemicyanine indicator comprises an iminium cation and a sulfonate anion; introducing the hemicyanine indicator to a solution containing an amount of sulfite, wherein the hemicyanine indicator reacts with the sulfite and causes a change in fluorescence of the solution wherein the change of fluorescence is based upon a reaction of sulfite with the alpha, beta-unsaturated iminium group of the hemicyanine indicator; and measuring the amount of sulfite in the solution by measuring an intensity of the fluorescence, wherein the fluorescence intensity is correlated to a concentration of the sulfite in the solution. The following is an example hemicyanine indicator for detection of sulfite:

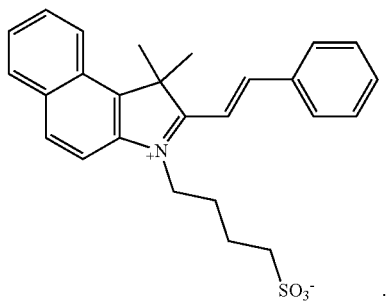

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
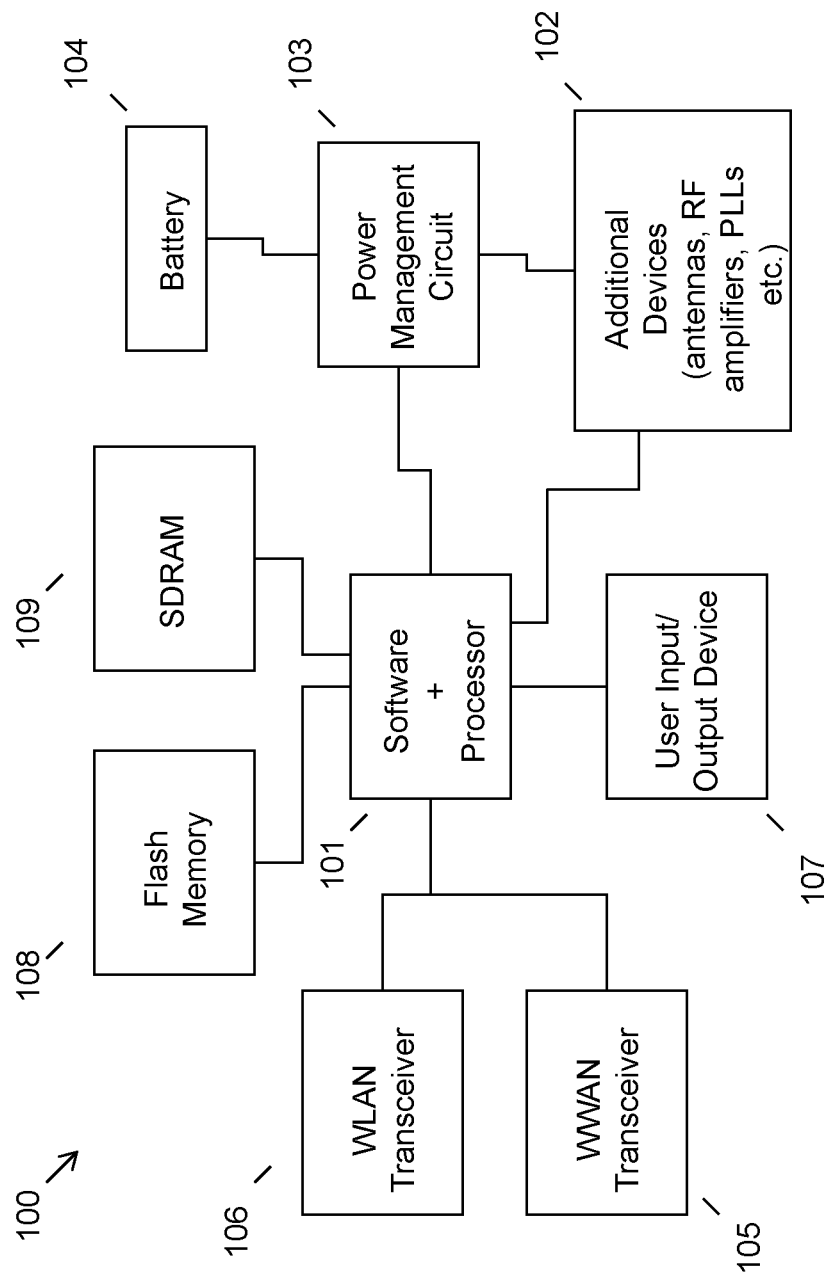
FIG. 1 illustrates an example of computer circuitry.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

Conventional methods of sulfite measurement in water may have some limitations. For example, sulfite measurement may be used to determine the quality of water. High concentrations of sulfite may be harmful to animals, humans, and/or plants. Accordingly, as another example, a user or entity may want the sulfite in a body of water to be under a particular threshold, therefore, the user may measure the sulfite in order to determine if the amount of sulfite is under that threshold.

A standard for sulfite measurement in water is iodometric titration. The iodometric titration method may detect sulfite in the range of 0-500 parts per million (ppm). Another sulfite detection method may be the HPT 430 method (available from Hach Company in Europe) which may have a sulfite detection range in a range of 0.1-5 ppm. However, these methods are not able to detect sulfite in an ultra low-range (ULR). ULR ranges may be measured in terms of parts per billion (ppb).

Other methods to measure sulfite may be used to detect low sulfite concentrations. However, these methods also have limitations. For example, a levulinate ester approach may be used. Although a level of detection of approximately 200 ppb may be achieved, the levulinate ester approach requires a co-solvent. The co-solvent may be DMSO (DMSO=dimethyl sulfoxide) which may not be preferable for some applications. Additionally there may be issues with hydrolysis for levulinate esters. A further example of sulfite detection method may be the use of an alpha, beta-unsaturated carbonyl with a related probe. And although a level of detection may be approximately 10 ppb, a cosolvent such as DMF (DMF=N,N-dimethylformamide) may be necessary which is not suited for all applications. Therefore, current methods, systems and kits for sulfite measurement using the iodometric titration, HPT 430 method, and others mentioned are limited due their inability to detect sulfite in the ppb range without using organic co-solvents. Once again, if additional reagents are used, such as solvents, then additional steps and/or toxic and expensive chemicals are required.

Accordingly, an embodiment provides a system and method for measuring sulfite at ultra low range (ULR) concentrations. In an embodiment, the method may not use traditional iodometric titration and HPT 430 methodologies. In an embodiment, the method may detect sulfite in concentrations ranging from approximately 0-800 parts per billion (ppb). In an embodiment, the method may use a fluorometric method. The indicator to give a fluorescent signal may be a hemicyanine indicator. In an embodiment, the fluorescence may be correlated to ULR detection of sulfite. The hemicyanine indicator may comprise a cation and an anion. The cation may be iminium. The anion may be sulfonate. In an embodiment, the fluorescent intensity may be correlated to a concentration of an amount of sulfite in a solution. The following is an example hemicyanine indicator for detection of sulfite:

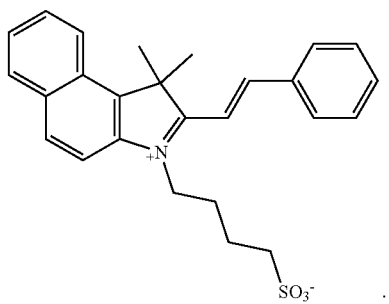

The illustrated example embodiments will be best understood by reference to the figures. The following description is intended only by way of example, and simply illustrates certain example embodiments.

While various other circuits, circuitry or components may be utilized in information handling devices, with regard to an instrument for measurement of sulfite according to any one of the various embodiments described herein, an example is illustrated in FIG. 1. Device circuitry 100 may include a measurement system on a chip design found, for example, a particular computing platform (e.g., mobile computing, desktop computing, etc.) Software and processor(s) are combined in a single chip 101. Processors comprise internal arithmetic units, registers, cache memory, busses, I/O ports, etc., as is well known in the art. Internal busses and the like depend on different vendors, but essentially all the peripheral devices (102) may attach to a single chip 101. The circuitry 100 combines the processor, memory control, and I/O controller hub all into a single chip 101. Also, systems 100 of this type do not typically use SATA or PCI or LPC. Common interfaces, for example, include SDIO and I2C.

There are power management chip(s) 103, e.g., a battery management unit, BMU, which manage power as supplied, for example, via a rechargeable battery 104, which may be recharged by a connection to a power source (not shown). In at least one design, a single chip, such as 101, is used to supply BIOS like functionality and DRAM memory.

System 100 typically includes one or more of a WWAN transceiver 105 and a WLAN transceiver 106 for connecting to various networks, such as telecommunications networks and wireless Internet devices, e.g., access points. Additionally, devices 102 are commonly included, e.g., a transmit and receive antenna, oscillators, PLLs, etc. System 100 includes input/output devices 107 for data input and display/rendering (e.g., a computing location located away from the single beam system that is easily accessible by a user). System 100 also typically includes various memory devices, for example flash memory 108 and SDRAM 109.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data. The disclosed system may be used in an embodiment to perform measurement of sulfite of an aqueous sample.

Figure 2:
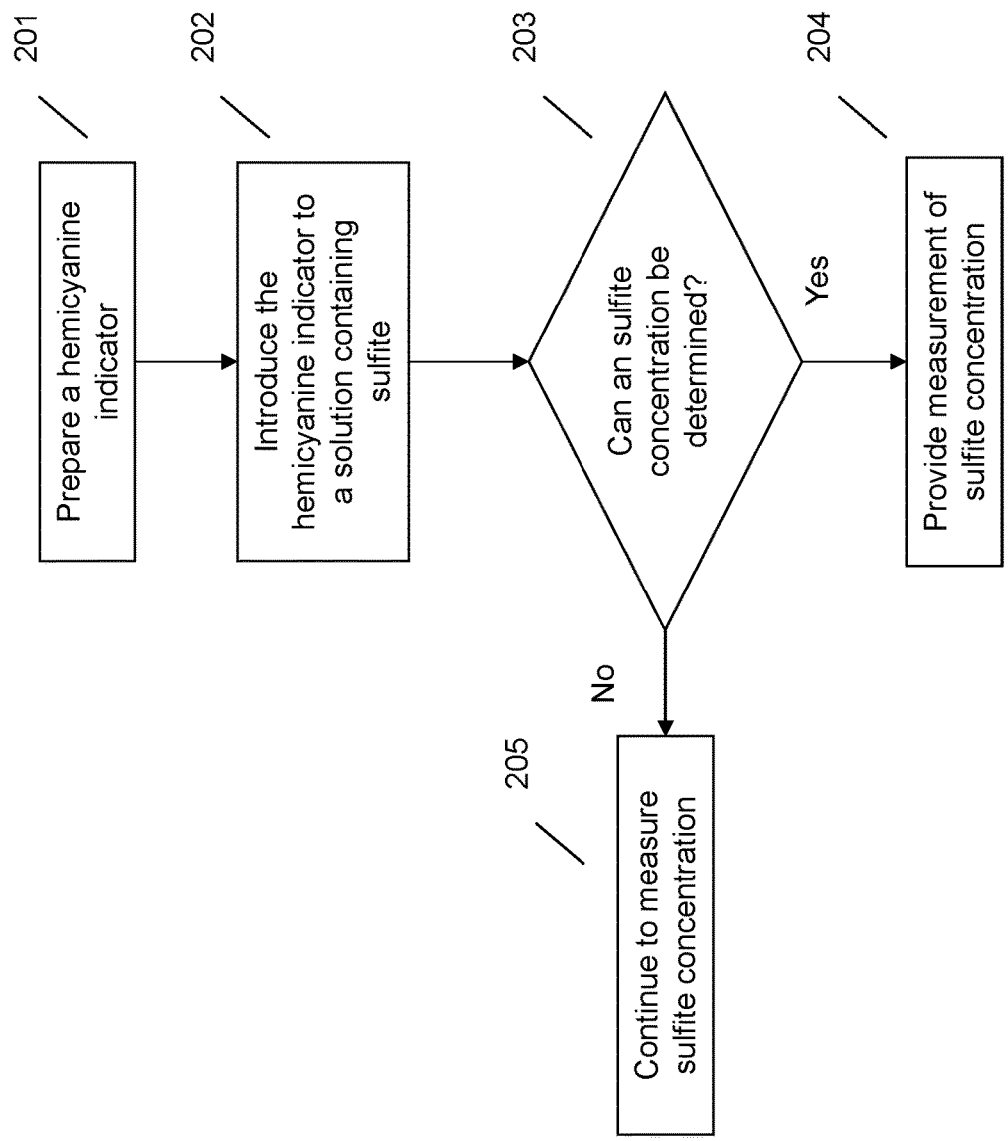
FIG. 2 illustrates a flow diagram of an example sufite measuring system.

Referring to FIG. 2, an example system and method for detection of sulfite in solution is illustrated. In an embodiment, a hemicyanine indicator may be prepared. The hemicyanine indicator may be introduced to a solution containing sulfite. In an embodiment, hemicyanine indicator may comprise a cation and an anion. The cation may be iminium. The anion may be sulfonate. In an embodiment, the hemicyanine indicator in the presence of sulfite may cause a change in fluorescence intensity of the hemicyanine indicator. The change of fluorescent intensity may be correlated to a concentration of sulfite in the solution. The hemicyanine indicator may be water soluble. Alternatively or additionally, the hemicyanine indicator may be soluble in another solvent.

Figure 3:
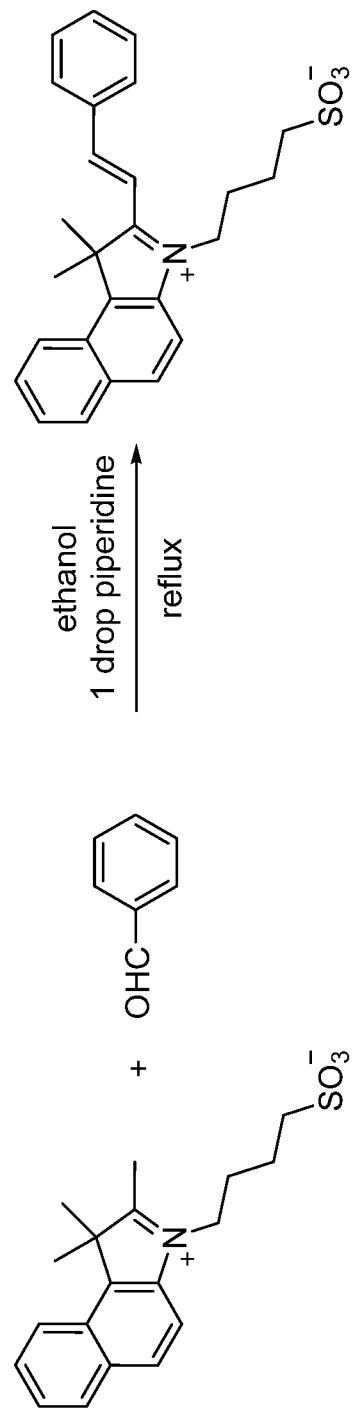
FIG. 3 illustrates a synthesis scheme of an example hemicyanine indicator for detection of sulfite.

At 201, in an embodiment, a hemicyanine indicator may be prepared. In an embodiment, hemicyanine indicator may comprise a cation and an anion. The cation may be iminium. The anion may be sulfonate. Referring to FIG. 3, an example reaction of the hemicyanine indicator is illustrated. In an embodiment, the synethesis reaction may be in the presence of a solvent. The solvent may be ethanol. In an embodiment, the synthesis reaction of the hemicyanine indicator may include piperidine. The synthesis reaction may be a reflux reaction. The synthesis reaction may require heat and/or the use of a condensing vessel. In an embodiment, the hemicyanine indicator may detect sulfite in the ultra low range of approximately 0-800 ppb. In an embodiment, a solution may be mostly water without any organic co-solvent At 202, in an embodiment, the hemicyanine indicator may be introduced into a solution. The solution may contain sulfite. The solution may be an aqueous sample which may include a sample from a natural body of water, a holding tank, a processing tank, a pipe, or the like. The solution may be in a continuous flow, a standing volume of liquid, or any combination thereof. In one embodiment, the solution may be introduced to the hemicyanine indicator, for example, a test chamber of the measurement device. Introduction of the solution into the measurement device may include placing or introducing the solution into a test chamber manually by a user or using a mechanical means, for example, gravity flow, a pump, pressure, fluid flow, or the like. For example, a water sample for sulfite testing may be introduced to a measurement or test chamber using a pump. In an embodiment, valves or the like may control the influx and efflux of the solution into or out of the one or more chambers, if present.

Figure 4:
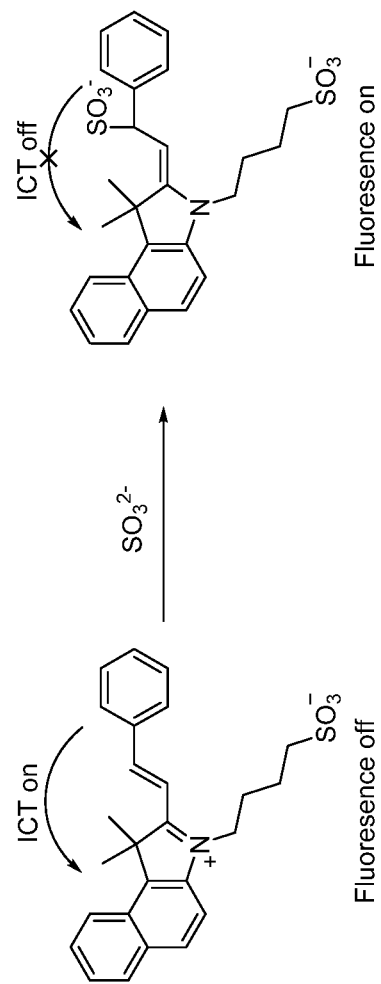
FIG. 4 illustrates a chemical equation of an example hemicyanine indicator for detection of sulfite.

Referring to FIG. 4, a change in fluorescence intensity of the hemicyanine indicator may occur in the presence of sulfite. For example, in the absence of sulfite the hemicyanine indicator is in a non-fluorescent state. The non-fluorescence state may be based upon an intramolecular charge transfer of the hemicyanine indicator. As another example, the hemicyanine indicator in the presence of sulfite may be in a fluorescent state. The fluorescent state may be based upon a reaction of sulfite with the alpha, beta-unsaturated iminium group of the hemicyanine indicator. The hemicyanine indicator in a solution of sulfite may have a fluorescence intensity correlated to an amount of sulfite in a solution. For example, in a solution some portion of the hemicyanine indicator may be fluorescent while another portion of the hemicyanine indicator may be non-fluorescent.

Additionally or alternatively, the measurement device may be present or introduced in a volume of the solution. The measurement device is then exposed to the volume of solution where it can perform measurements. The system may be a flow-through system in which a solution and/or reagents are automatically mixed and measured. Once the sample is in contact with the measurement system, the system may measure the sulfite of the sample, as discussed in further detail herein. In an embodiment, the measurement device may include one or more chambers in which the one or more method steps may be performed.

In an embodiment, the pH of the solution may be maintained. For example, the pH may be adjusted or titrated to around a pH of 7.5. The hemicyanine indicator may be approximately 350 μL water saturated solution of the indicator. In an embodiment, a buffer may be added. The buffer may be in a concentration of 75 mM. Saline may be added in the concentration range of 0-25 mM. In an embodiment, the reaction time of the hemicyanine indicator with sulfite may be adjusted. The reaction time may be adjusted based upon a reaction temperature. For example, the reaction time may be approximately 4 minutes at 25 degrees Celsius. As another example, the reaction time may be 10 minutes at 20 degrees Celsius. An approximate range of detection of sulfite is between 0-800 ppb.

Figure 5:
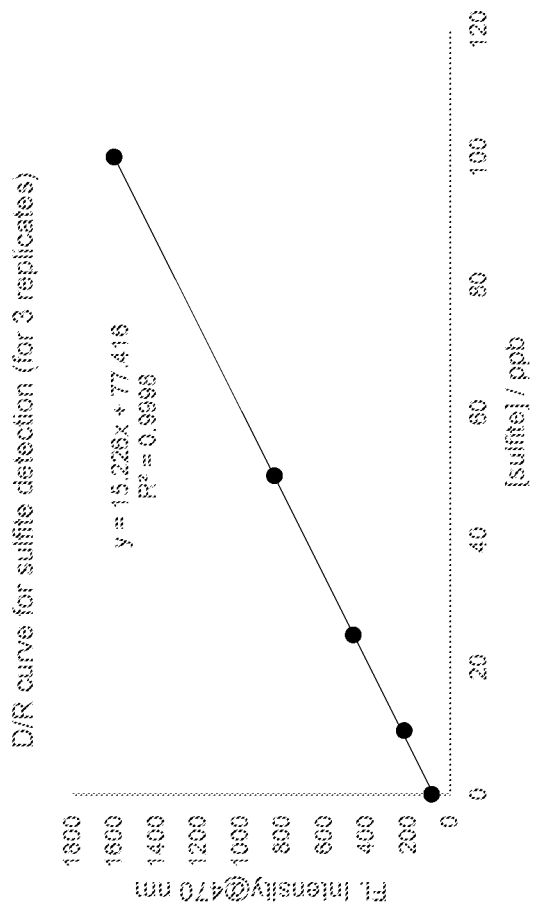
FIG. 5 illustrates an example fluorescence intensity measurement using a hemicyanine indicator.

At 203, in an embodiment, the system and method may determine if a sulfite concentration may be determined. In an embodiment, the presence of sulfite in an aqueous solution may cause a shift in the wavelength of the hemicyanine indicator. Examples of this shift in fluorescence intensity and dose response curves for a hemicyanine indicator may be illustrated in FIG. 5. Therefore, the fluorescence intensity, of a solution containing sulfite may be correlated to the concentration of the sulfite in the aqueous solution. Fluorescence curves may be generated for a range of sulfite concentrations, for different hemicyanine indicator, for any different condition that may affect absorption or fluorescence values (e.g., temperature, sample content, turbidity, viscosity, measurement apparatus, aqueous sample chamber, etc.), or the like.

Alternatively or additionally, sulfite concentration measurement may be at periodic intervals set by the user or preprogrammed frequencies in the device. Measurement of sulfite by a device allows for real time data with very little human involvement in the measurement process. Cleaning of the fluorometric chamber may be required at an unspecified time interval. A programmed calibration curve may be entered into the device.

A chamber, vessel, cell, chamber, or the like may contain an aqueous sample, at least one hemicyanine indicator, and associated reagents such as buffers, reagents, saline, or the like. A device may contain one or more bottles of reagents which contain necessary reagents. The reagents contained in the one or more bottles may be pump fed or gravity fed. The flow of the reagents may be metered to ensure proper volume delivery to the measurement cell. The aqueous sample may be fed through a pressured inlet, a vessel, or the like. The aqueous sample may be introduced into the measurement chamber by a pump or gravity fed. The sampling device may be in series or parallel to an aqueous flow. The device may have a system to ensure proper mixing of the aqueous sample, hemicyanine indicator, and related reagents.

The fluorescent intensity or sulfite concentration may be an output upon a device in the form of a display, printing, storage, audio, haptic feedback, or the like. Alternatively or additionally, the output may be sent to another device through wired, wireless, fiber optic, Bluetooth®, near field communication, or the like. An embodiment may use an alarm to warn of a measurement or concentration outside acceptable levels. An embodiment may use a system to shut down water output or shunt water from sources with unacceptable levels of an analyte. For example, an analyte measuring device may use a relay coupled to an electrically actuated valve, or the like.

At 205, in an embodiment, if a concentration of sulfite cannot be determined, the system may continue to measure sulfite. Additionally or alternatively, the system may output an alarm, log an event, or the like.

If a concentration of sulfite can be determined, the system may provide a measurement of sulfite concentration at 204. The system may connect to a communication network. The system may alert a user or a network. This alert may occur whether a sulfite measurement is determined or not. An alert may be in a form of audio, visual, data, storing the data to a memory device, sending the output through a connected or wireless system, printing the output or the like. The system may log information such as the measurement location, a corrective action, geographical location, time, date, number of measurement cycles, or the like. The alert or log may be automated, meaning the system may automatically output whether a correction was required or not. The system may also have associated alarms, limits, or predetermined thresholds. For example, if a sulfite concentration reaches a threshold. Alarms or logs may be analyzed in real-time, stored for later use, or any combination thereof.

The various embodiments described herein thus represent a technical improvement to conventional sulfite measurement techniques. Using the techniques as described herein, an embodiment may use a hemicyanine indicator to measure sulfite in solution. This is in contrast to conventional techniques with limitations mentioned above. Such techniques provide a faster and more accurate method for measuring sulfite in an aqueous or liquid solution.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand held measurement device, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A composition for measuring sulfite in a solution, comprising:
   a hemicyanine indicator having the chemical formula:

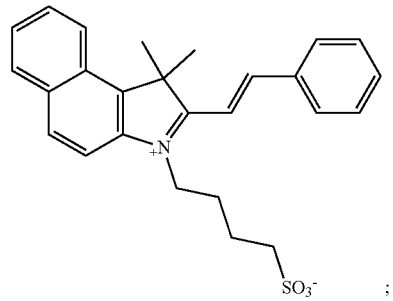

2. A system for measuring sulfite in a solution, comprising:
   a hemicyanine indicator having the chemical formula:

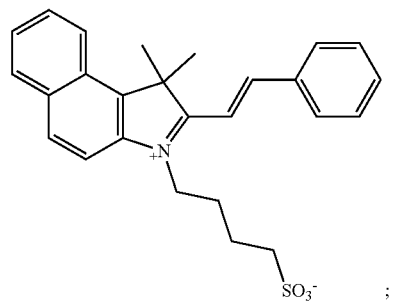

and
   a measurement device using the hemicyanine indicator to measure sulfite in the solution.

3. The system of claim 2, wherein the solution is titrated to a pH around a pH of 7.5.

4. The system of claim 2, wherein the solution is heated.

5. The system of claim 2, comprising a display output for the sulfite measurement.

6. A method for measuring sulfite in a solution, comprising:
   preparing a hemicyanine indicator, wherein the hemicyanine indicator comprises the chemical formula:

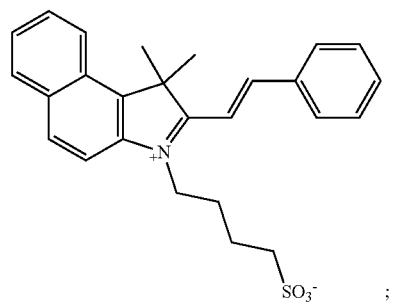

introducing the hemicyanine indicator to a solution containing an amount of sulfite, wherein the hemicyanine indicator reacts with the sulfite and causes a change in fluorescence of the solution; and measuring the amount of sulfite in the solution by measuring an intensity of the fluorescence.

7. The method of claim 6, wherein the change of fluorescence is based upon a reaction of sulfite with the alpha, beta-unsaturated iminium group of the hemicyanine indicator.

8. The method of claim 6, wherein the measuring further comprises titrating a pH of the solution to around a pH of 7.5.

9. The method of claim 6, wherein the intensity of the fluorescence is correlated to a concentration of the sulfite in the solution.

10. The method of claim 6, further comprising adding at least one of: a saline buffer and a phosphate buffer to the solution.

11. The method of claim 6, wherein the introducing further comprises heating the solution.

* * * * *